United States Patent [19]

Shen et al.

[11] 3,932,498

[45] Jan. 13, 1976

[54] 3-INDENYL-γ-(KETOBUTYRIC)-ACID COMPOUNDS

[75] Inventors: Tsung-Ying Shen, Westfield; Howard Jones, Holmdel; Michael W. Fordice, Cranford, all of N.J.

[73] Assignee: Merck & Co., Inc., Rahway, N.J.

[22] Filed: Feb. 23, 1973

[21] Appl. No.: 335,220

Related U.S. Application Data

[63] Continuation-in-part of Ser. No. 108,628, Jan. 21, 1971, abandoned.

[52] U.S. Cl....... 260/515 A; 260/240 R; 260/247.1; 260/448 R; 260/465 D; 260/469; 260/470; 260/471 R; 260/473 F; 260/475 SC; 260/479 R; 260/501.1; 260/501.11; 260/501.12; 260/501.16; 260/501.21; 260/516; 260/520; 260/546; 260/558 S; 260/559 T; 260/599; 260/609 D; 260/618 D; 260/618 F; 424/248; 424/274; 424/267; 424/250

[51] Int. Cl.² ............. C07C 149/28; C07C 147/107; C07C 147/14

[58] Field of Search............ 260/515 R, 465 D, 470, 260/515 A, 516, 546, 520, 479 R

[56] References Cited

UNITED STATES PATENTS 3,732,292   5/1973   Hinkley et al. ..................... 260/515

*Primary Examiner*—James A. Patten
*Attorney, Agent, or Firm*—Mario A. Monaco; Harry E. Westlake, Jr.

[57] ABSTRACT

New substituted indene acids and non-toxic pharmaceutically acceptable amides, esters and salts derived therefrom. The substituted indene acids disclosed herein have anti-inflammatory, anti-pyretic and analgesic activity. Also included herein are methods of preparing said indene acid compounds, pharmaceutical compositions having said indene acid compounds as an active ingredient and methods of treating inflammation by administering these particular compositions to patients.

7 Claims, No Drawings

3-INDENYL-γ-(KETOBUTYRIC)-ACID COMPOUNDS

CROSS REFERENCES

This application is a continuation-in-part of application Ser. No. 108,628 filed Jan. 21, 1971 now abandoned.

SUMMARY OF THE INVENTION

This invention relates to new substituted indenyl acid compounds and processes for producing the same. More specifically, this invention relates to compounds having the following general formula:

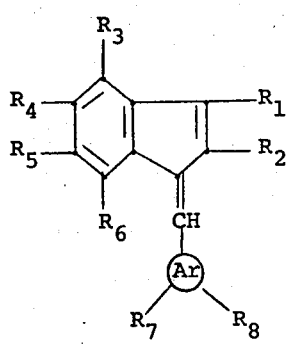

(I)

wherein
$R_1$ is
—CH(OH)CH$_2$CH$_2$COM,
—CH$_2$CH(OH)CH$_2$COM,
—CH$_2$CH$_2$CH(OH)COM,

wherein
Ar is aryl or heteroaryl;
$R_2$ is hydrogen, alkyl, alkenyl, alkynyl or haloalkyl;
$R_3$, $R_4$, $R_5$ and $R_6$ each may be hydrogen, alkyl, acyloxy, alkoxy, nitro, amino, acylamino, alkylamino, dialkylamino, dialkylaminoalkyl, sulfamyl, alkylthio, mercapto, hydroxy, hydroxyalkyl, alkylsulfonyl, halogen, cyano, carboxyl, carboalkoxy, carbamido, haloalkyl, cycloalkyl, cycloalkoxy, alkenyloxy, acyl, alkenyl or alkynyl;
$R_7$ is alkylsulfinyl, alkylsulfonyl or alkylthio ($C_{1-5}$alkylthio);
$R_8$ is hydrogen, halogen, hydroxy, alkoxy or haloalkoxy; and
M is hydroxy, loweralkoxy, substituted loweralkoxy, amino, alkylamino, dialkylamino, N-morpholino, hydroxyalkylamino, polyhydroxyalkylamino, dialkylaminoalkylamino, aminoalkylamino or OMe in which Me is a cation of a pharmaceutically acceptable salt;
provided that at least one of $R_3$, $R_4$, $R_5$ and $R_6$ is not hydrogen.

In the more preferred aspect of this invention, $R_1$ is —CH$_2$-CH(OH)CH$_2$COM or

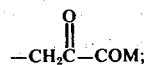

Ar is phenyl; $R_2$ is hydrogen or $C_{1-5}$ alkyl; $R_3$, $R_4$, $R_5$ and $R_6$ are each hydrogen, $C_{1-5}$ alkyl, $C_{1-5}$ alkoxy, halogen (fluoro, chloro), cyano, $C_{1-5}$ alkanoyl, $C_{2-5}$ alkenyloxy or $C_{1-5}$ alkanoyloxy, at least two of $R_3$, $R_4$, and $R_6$ being hydrogen at any one time; $R_7$ is $C_{1-5}$ alkylsulfinyl or $C_{1-5}$ alkylsulfonyl, (especially alkylsulfinyl); $R_8$ is hydrogen, hydroxy, $C_{1-5}$ alkoxy, $C_{1-5}$ haloalkoxy or fluoro; M is hydroxy, $C_{1-5}$alkoxy, $C_{1-5}$ alkanoyloxy-$C_{1-5}$ alkoxy or OMe, and especially hydroxy.

In the most preferred aspect of this invention, $R_1$ is —CH$_2$CH(OH)—CH$_2$COM or

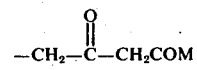

and especially —CH$_2$—CH(OH)—CH$_2$COM; $R_2$ is $C_{1-5}$ alkyl; $R_3$ is hydrogen; $R_4$, $R_5$ and $R_6$ are each hydrogen, fluoro, $C_{1-5}$ alkoxy, $C_{1-5}$ alkenyloxy or cyano, at least one of $R_4$, $R_5$ and $R_6$ being hydrogen at any one time; $R_7$ is $C_{1-5}$ alkylsulfinyl; $R_8$ is hydrogen, M is hydroxy and Ar is phenyl.

Representative compounds of this invention are as follows:

5-Fluoro-2-methyl-1-(4'-methylsulfinylbenzylidene)-3-indenyl-γ-(α-hydroxybutyric) acid
5-Fluoro-1-(4'-methylsulfinylbenzylidene)-3-indenyl-γ-(γ-ketobutyric) acid
5-Fluoro-2-methyl-1-(4'-methylsulfinylbenzylidene)-3-indenyl-γ-(β-hydroxybutyric) acid
5-Fluoro-2-methyl-1-(4'-methylsulfinylbenzylidene)-3-indenyl-γ-(β-ketobutyric) acid
5-Fluoro-2-methyl-1-(4'-methylsulfinylbenzylidene)-3-indenyl-γ-(α-hydroxybutyric) acid
5-Fluoro-2-methyl-1-(4'-methylsulfinylbenzylidene)-γ-(α-ketobutyric) acid and the corresponding amides, esters and pharmaceutically acceptable salts thereof.

It should be noted that the compounds of this invention may be isomerized into their cis and trans isomers by procedures well known in the art. It should be further noted that the cis isomer of the compounds of this invention is substantially more active than the trans isomer. Accordingly, it is to be understood that reference throughout the specification and appended claims to the compounds of this invention is intended to encompass not merely the compounds per se but includes their geometric isomers (cis, trans).

It should be further noted by one skilled in the art that the alkylsulfinyl derivatives of this invention are racemic mixtures of optically active enantiomorphs which may be resolved into their (+) and (−) forms by techniques well known in the art. Furthermore, when R and R' are different, an additional asymmetric atom results which gives rise to two additional enantiomorphs, which are also considered to be within the scope of the invention.

One skilled in the art should further note that some of the compounds of this invention are polymorphic and have different crystalline structures, melting points and solubility characteristics.

This invention also relates to a method of treating pain, fever or inflammation in patients using a compound of Formula I, particularly an especially preferred compound as the active constituent.

The compounds of the instant invention can be used to treat inflammation by reducing inflammation and relieving pain in such diseases as rheumatoid arthritis, osteoarthritis, gout, infectious arthritis and rheumatic fever.

The compounds of Formula I also have anti-pyretic and analgesic activity and would be administered and used in the same manner and in the same dosage ranges as if they were being used to treat inflammation as discussed further on.

The treatment of inflammation in accordance with the method of the present invention is accomplished by topically, orally, rectally or parenterally administering to patients a composition of a compound of Formula I, particularly the especially preferred compounds in a non-toxic pharmaceutically acceptable carrier.

The non-toxic pharmaceutical carrier may be, for example, either a solid or a liquid. Exemplary of solid carriers are lactose, corn starch, gelatin, talc, sterotix, stearic acid, magnesium stearate, terra alba, sucrose, agar, pectin, cab-o-sil and acacia. Exemplary of liquid carriers are peanut oil, olive oil, seasame oil and water. Similarly, the carrier or diluent may include a time delay material such as glyceryl monostearate or glyceryl distearate alone or with a wax.

Several pharmaceutical forms of the therapeutically useful compositions can be used. For example, if a solid carrier is used, the compositons may take the form of tablets, capsules, powders, troches or lozenges prepared by standard pharmaceutical techniques. If a liquid carrier is used, the preparation may be in the form of a soft gelatin capsule, a syrup, an aqueous solution or a liquid suspension. Suppositories may be prepared in a conventional manner by mixing the compounds of this invention with a suitable non-irritating excipient which is solid at room temperature, but liquid at the rectal temperature. Such materials are cocoa butter and polyethylene glycol. Gels and lotions for topical application may be prepared in conventional manners.

The active compounds of Formula I and of the compositions of this invention are administered in an amount sufficient to treat inflammation, that is to reduce inflammation. Advantageously, the compositions will contain the active ingredient; namely, the compounds of Formula I in an amount of from about 0.1 mg. to 50 mg. per kg. body weight per day (5 mg. to 3.5 g. per patient per day), preferably from about 1 mg. to 15 mg./kg. body weight per day (50 mg. to 1 g. per patient per day).

The method of treatment of this invention comprises administering to a patient (animal or human) a compound of Formula I, particularly an especially preferred compound admixed with a non-toxic pharmaceutical carrier such as exemplified above. The compounds of Formula I and particularly the especially preferred compounds will be administered in an amount of from 0.1 mg. to 50 mg./kg. body weight per day, preferably from about 1 mg. to about 15 mg. per kilogram body weight per day. The most rapid and effective anti-inflammatory effect is obtained from oral administration of a daily dosage of from about 1 to 15 mg./kg. per day. It should be understood, however, that although preferred dosage ranges are given, the dose level for any particular patient depends upon the activity of the specific compound employed. Also, many other factors that modify the actions of drugs will be taken into account by those skilled in the art in the therapeutic use of medicinal agents, particularly those of Formula I, for example, age, body weight, sex, diet, time of administration, route of administration, rate of excretion, drug combination, reaction sensitivities and severity of the particular disease.

In the preparation of the compounds of this invention, the starting material is a $\beta$-aryl propionic acid. This compound is prepared according to the procedure shown in Flow Sheet I which illustrates several alternative routes. Thus, a substituted benzaldehyde may be condensed with a substituted acetic ester in a Claisen Reaction or with an $\alpha$-halogenated propionic ester in a Reformatsky Reaction. The resulting unsaturated ester is reduced and hydrolyzed to give the benzyl propionic acid starting material. Alternatively, a substituted malonic ester in a typical malonic ester synthesis and acid hydrolysis of the resulting substituted ester yields the benzyl propionic acid directly or the benzaldehyde may be reacted with propionic anhydride in a reducing medium to form the benzyl propionic acid.

Equivalents:
  X is halogen, usually Cl or Br;
  E is an esterifying group, usually methyl, ethyl, or benzyl;
  $R_2$ is alkyl, alkenyl, alkynyl or haloalkyl; and
  $R_3$, $R_4$, $R_5$, and $R_6$ each may be hydrogen, alkyl, acyloxy, alkoxy, nitro, amino, acylamino, alkylamino, dialkylamino, dialkylaminoalkyl, sulfamyl, alkylthio, mercapto, hydroxy, hydroxyalkyl, alkylsulfonyl, halogen, cyano, carboxy, carboalkoxy, carboxamido, haloalkyl, cycloalkyl, cycloalkoxy, alkenyloxy, acyl, alkenyl or alkynyl;

Reagents:
  1. Zn dust in anhydrous inert solvent such as benzene and ether.
  2. $KHSO_4$ or p-toluene sulfonic acid.
  3. $NaOC_2H_5$ in anhydrous ethanol at room temperature.
  4. $H_2$, palladium on charcoal, 40 p.s.i., room temperature.
  5. NaOH in aqueous alcohol at 20°–100°.
  6. $NaOC_2H_5$ or any other strong base, such as NaOH or K-t-butoxide.
  7. Acid.

1. Preparation of $\beta$-arylpropionic acid starting material.

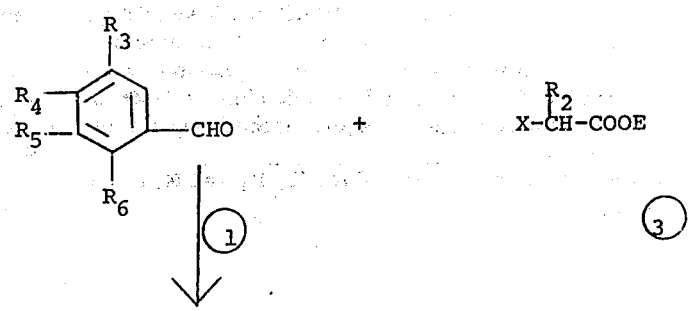

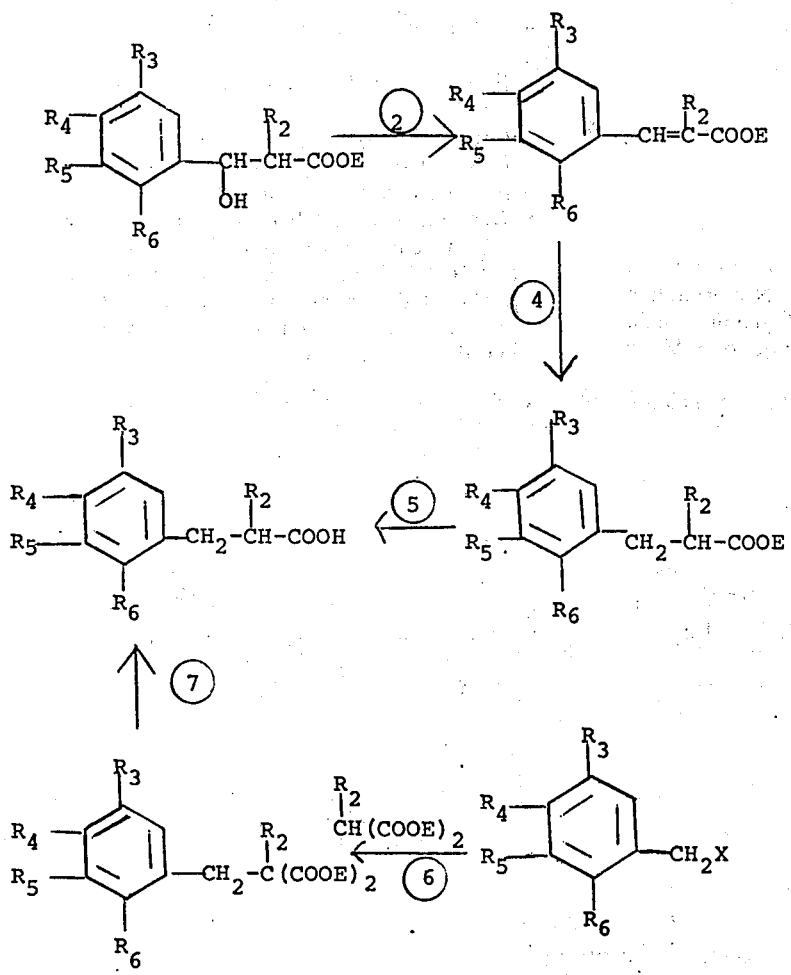

In the preparation of the compounds of the instant invention, again a number of routes are possible, as shown in Flow Sheet II. The first step in ring closure of the α-aryl propionic acid to form an indanone which may be carried out by a Friedel-Crafts Reaction using a Lewis acid catalyst or by heating with polyphosphoric acid. The indanone may be condensed with an α-halo ester in the Reformatsky Reaction to introduce an aliphatic acid side chain by replacing the carbonyl group. Alternatively, this introduction can be carried out by use of a Wittig Reaction in which the reagent is an α-triphenylphosphinyl ester, a reagent which replaces the carbonyl with a double bond to a carbon. This is immediately rearranged into the indene. If the Reformatsky Reaction route is used, the intermediate 3-hydroxy-3aliphatic acid derivative must be dehydrated to the indene. In the preparation of the α-(β-hydroxybutyric) acid compounds, the indenyl-3-acetic acid ester is reduced to the corresponding alcohol, which in turn is oxidized to the alcohol compound. This latter compound is then treated with a halo acetic ester to form the α-(β-hydroxybutyric) acid ester. The corresponding α-(β-ketobutyric) acid ester is prepared by oxidation of the α-(β-hydroxybutyric) acid ester. The indenyl-3-α-(α-ketobutyric) acid compound is prepared by condensation of the indanone with a 3-halo butyric acid ester and subsequent reaction of the acetylinic compound to form the α-ketobutyric acid compound. The indenyl-3-α-(α-hydroxybutyric) acid compound may be readily prepared by reduction of the corresponding indenyl-3-α-(α-ketobutyric) acid compound. The introduction of the 1-substituent is carried out in one of two ways. The first is the direct reaction of the indene with the aldehyde of the structural characteristics defined, using a strong base as a catalyst and warming, if necessary, to form the carbanion. The reaction can be carried out in a number of solvents such as polar solvents like dimethoxyethane, aqueous methanol, pyridine, liquid ammonia, dimethylformamide and the like, or even in non-polar solvents such as benzene, etc. Alternatively, an indanone can be brominated and then dehydrogen-brominated to an indenone and the indenone carbonyl replaced by the substituent using the α-triphenyl-phosphinyl compounds of the desired structure. Note that a loweralkyl ester of the desired compound is formed in the third step. This ester can then be hydrolyzed to give the free acids and oxidized to give the sulfoxides and sulfones from which the salts, other esters and the amides may be formed. The keto substituted acid side chains may be prepared by oxidizing the hydroxy acid side chain.

Equivalents:

X, E, $R_2$, $R_3$, $R_4$, $R_5$ and $R_6$ are the same as in Flow Sheet I;

Ar is aryl or heteroaryl;

$R_1$ is

—CH(OH)CH$_2$CH$_2$COM,
—CH$_2$CH(OH)CH$_2$COM,
—CH$_2$—CH$_2$—CH(OH)COM

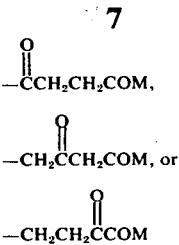

wherein
M is hydroxy, loweralkoxy, substituted loweralkoxy, amino, alkylamino, dialkylamino, N-morpholino, hydroxyalkylamino, polyhydroxyalkylamino, dialkylaminoalkylamino, aminoalkylamino or OMe in which Me is a cation;
$R_8$ is hydrogen, halogen, hydroxy, alkoxy or haloalkoxy; and $R_9$ is hydrogen or loweralkyl.

Reagents:
1. Friedel-Crafts Reaction using a Lewis Acid catalyst.
2. Heat with polyphosphoric acid.
3. Reformatsky Reaction: Zn in inert solvent, heat.
4. p-Toluene sulfonic acid and $CaCl_2$ or $I_2$ at 200°.
5. Reaction with aldehyde or ketone, using strong base as catalyst (K-t-butoxide or any alkoxide, NaOH, KOH, $NaNH_2$, etc.), warming if necessary to form the carbanion in solvents as liquid ammonia, dimethylformamide, 1,2-dimethoxyethane, pyridine, aqueous alcohol, etc.

II. Preparation of α-(1-substituted-benzylidenyl)-3-indenyl)aliphatic acids.

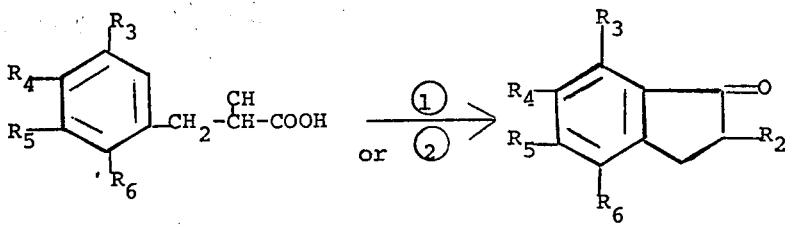

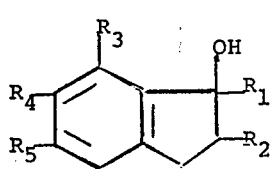

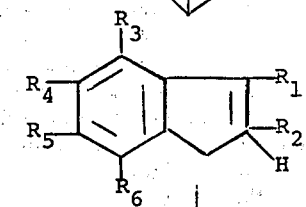

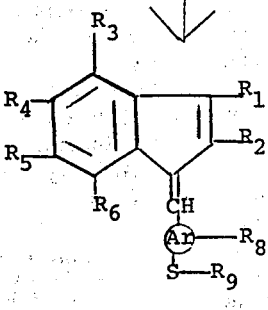

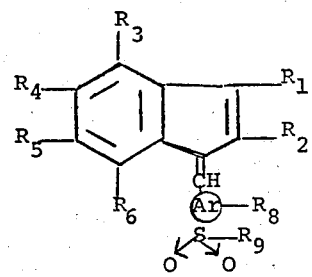

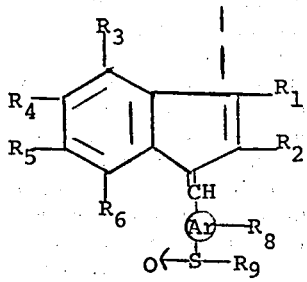

Although the syntheses described may produce esters of the acids of this invention, some desired esters are more easily obtained by forming a simple ester of the final acid, hydrolyzing to the free acid and re-esterifying. The simple loweralkyl or benzyl esters are usually the ones used in the synthesis of the compounds. Other esters are more desirable from the standpoint of therapeutic utility of the compounds, such as the methoxymethyl, diethylaminoethyl, dimethylaminoethyl, dimethylaminopropyl, diethylaminopropyl, N-pyrollidinylethyl, N-piperidinylethyl, N-morpholinylethyl, N-ethyl-2-piperidinylethyl, N-pyrollidinylmethyl, N-methyl-2-pyrollidinylmethyl, 4-methyl-1-piperazinylethyl, methoxyethyl, ethoxyethyl and the like. These are mostly prepared from the corresponding alcohol and the indenyl acid.

The amides, both the simple amide and the substituted amides, are similarly prepared from the indenyl acids and the corresponding amines. Especially useful therapeutically are the morpholide, the bis(hydroxyethyl)amide and the like.

Similarly, salts are obtained by neutralizing the indenyl acids with bases or by methathesis of other salts. Especially useful are the metallic salts such as the alkali metal or alkaline earth salts and the amine and quaternary ammonium salts, which are water soluble, but the heavy metal salts such as iron, aluminum, etc. are also useful for some purposes.

The following examples are presented to further illustrate the invention:

EXAMPLE 1

A. 5-Fluoro-2-methylindenyl-3-(β-ethanol)

9.8 G. of methyl 5-fluoro-2-methylindenyl-3-acetate in 75 ml. of ether is added with stirring to a suspension of 1.0 g. of lithium aluminum hydride in 50 ml. of ether during a 30 minute period. The reaction mixture is then held at reflux for 3 hours, cooled, and 50 ml. of methanol slowly added, followed by 50 ml. of water. The entire solution is filtered through celite and dried with anhydrous magnesium sulfate. The solution is filtered and concentrated to give an oil which solidifies, m.p. 64°–66°.

B. 5-Fluoro-2-methylindenyl-3-acetaldehyde 1.92 G. of the above alcohol in 50 ml. of a solution of 20 g. of chromium trioxide-bis-pyridyl complex in 300 ml. of methylene chloride is stirred at room temperature for 45 minutes. After this time the solution is filtered and the residue washed with ethyl acetate. The combined organic layers are poured into water (200 ml.) and more ethyl acetate is added until the organic layers are lighter than water. The organic layer is dried over anhydrous magnesium sulfate, filtered and evaporated to dryness to give a dark-red oil.

The oil is chromatographed on silica-gel (100 g.) and the aldehyde eluted with benzene. It is an oil with N.M.R. (in dimethyl sulfoxide):

| triplet | 0.37 (J = 1.5 c.p.s.) |
|---|---|
| multiplet | 2.5–3.3 |
| two broad singlets | 6.30 and 6.65 |
| singlet | 8.95 |

C. Methyl 5-fluoro-2-methyl-3-indenyl-γ-(β-hydroxybutyrate)

A mixture of 5-fluoro-2-methyl-3-indenylacetaldehyde (28.5 g., 0.15 mole), "activated" zinc dust (13.1 g., 0.20 mole), methyl bromoacetate (23.0 g., 0.15 mole) and a crystal of iodine in dry benzene (750 ml.) is refluxed for 5 hours. The mixture is poured into 5% sulfuric acid (750 ml.), extracted with ether, the ether extract dried (MgSO$_4$), and the ethereal solution concentrated. The crude ester is crystallized from methanol-n-hexane to yield methyl 5-fluoro-2-methyl-3-indenyl-γ-(β-hydroxybutyrate).

D. cis- and trans-5-Fluoro-2-methyl-1-(4′-methylthio-benzylidene)-3-indenyl-γ-(β-hydroxybutyric) Acids Powdered sodium methoxide (11 g., 0.20 mole) is added to a suspension of esters (27.8 g., 0.1 mole) from Example 1-C and methylthiobenzaldehyde (16.7 g., 0.11 mole) in methanol (200 ml.) under dry nitrogen. A clear solution results and this mixture is refluxed 1 hour. An equal volume of water is added and the refluxing continued for 30 minutes to complete saponification. The solution is cooled to room temperature (25°) and diluted with several volumes of water. Addition of 50% acetic acid (200 ml.) precipitates the product. The precipitate is separated by filtration, washed well with water and dried in vacuo over potassium hydroxide pellets. The crude product is taken up in methylene chloride and chromatographed over silica gel to separate cis- and trans- isomers, identifiable by integrating the 2-CH$_3$ signal in the N.M.R. spectrum.

E. cis-5-Fluoro-2-methyl-1-(4′-methylsulfinylbenzylidene)-3-indenyl-γ-(β-hydroxybutyric)-Acid To a solution of thio compound (3.84 g., 0.01 mole) from Example 1-D in methanol (100 ml.), acetone (100 ml.), and water (20 ml.) is added sodium periodate (11.3 g.) in water (20 ml.). The mixture is stirred for 24 hours at 25° under nitrogen after which the mixture is concentrated in vacuo to small volume. The concentrate is diluted with water, filtered, the precipitate washed and dried in air, then in vacuo at 50°. The residue is recrystallized from methanol-n-hexane to yield cis-5-fluoro-2-methyl-1-(4′-methylsulfinylbenzylidene)-3-indenyl-γ-(β-hydroxybutyric) acid.

Using the same reaction conditions and techniques the following indenyl-γ-(β-hydroxybutyric) acids are prepared from the indenyl ester.

| STARTING MATERIAL | PRODUCT |
|---|---|
| methyl 5,6-difluoro-2-methyl-indenyl-3-acetate | cis-5,6-difluoro-2-methyl-1-(4′-me |
| methyl 5-fluoro-6-methoxy-2-methylindenyl-3-acetate | cis-5-fluoro-6-methoxy-2-methyl-1-(4′-methylsulfinyl-benzylidene)-3-indenyl-γ-(β-hydroxybutyric) acid |
| methyl 5,7-difluoro-2-methyl indenyl-3-acetate | cis-5,7-difluoro-2-methyl-1-(4′-methylsulfinyl-benzylidene)-3-indenyl-γ-(α-hydroxybutyric) acid |

| | |
|---|---|
| methyl 5-cyano-2-methylindenyl-3-acetate | cis-5-cyano-2-methyl-1-(4'-methylsulfinylbenzylidene)-3-indenyl-γ-(β-hydroxybutyric) acid |
| methyl 5-methoxy-2-methyl-indenyl-3-acetate | cis-5-methoxy-2-methyl-1-(4'-methylsulfinylbenzylidene)-3-indenyl-γ-(β-hydroxybutyric) acid |
| methyl 5-allyloxy-2-methyl indenyl-3-acetate | cis-5-allyloxy-2-methyl-1-(4'-methylsulfinylbenzylidene)-3-indenyl-γ-(β-hydroxybutyric acid |
| methyl 5,6-difluoroindenyl-3-acetate | cis-5,6-difluoro-1-(4'-methylsulfinylbenzylidene)-3-indenyl-γ-(β-hydroxybutyric) acid |
| methyl 5-fluoro-6-methoxy-indenyl-3-acetate | cis-5-fluoro-6-methoxy-1-(4'-methylsulfinylbenzylidene)-3-indeny l-γ-(β-hydroxybutyric) acid |
| methyl 5,7-difluoroindenyl-3-acetate | cis-5,7-difluoro-1-(4.-methylsulfinylbenzylident)-3-indenyl-γ-(β-hydroxybutyric) acid |
| methyl 5-cyanoindenyl-3-acetate | cis-5-cyano-1-(4'-methylsulfinylbenzylidene)-3-indenyl-γ-(β-hydroxybutyric) acid |
| methyl-5-methoxyindenyl-3-acetate | cis-5-methoxy-1-(4'-methylsulfinylbenzylidene)-3-indenyl-γ-(β-hydroxybutyric) acid |
| methyl 5-allyloxyindenyl-3-acetate | cis-5-allyloxy-1-(4'-methylsulfinylbenzylidene)-3-indenyl-3-γ-(β-hydroxybutyric) acid |

EXAMPLE 2 cis-5-Fluoro-2-methyl-1-(4'-methylsulfinylbenzylidene)-3-indenyl-γ-(β-ketobutyric) Acid To a solution of the thio compound (3.84 g., 0.01 mole) from Example 1-D in 80% acetic acid (150 ml.) at 60° is added with stirring over 10 minutes 1.3 g. of 37 chromium trioxide. The mixture is maintained at 60°–65° with stirring for an additional 20 minutes. The mixture is poured into ice and water (200 g.), filtered, washed with water and the precipitate dried in air. The residue is recrystallized from methanol-n-hexane to yield cis-5-fluoro-2-methyl-1-(4'-methylsulfinylbenzylidene)-3-indenyl-γ-(β-ketobutyric) acid.

Using the same reaction conditions and techniques the following indenyl-γ-(β-ketobutyric) acids are obtained:

| STARTING MATERIAL | PRODUCT |
|---|---|
| cis-5,6-difluoro-2-methyl-1-(4'-methylthiobenzylidene)-3-indenyl-γ-(β-hydroxybutyric acid | cis-5,6-difluoro-2-methyl-1-(4'-methylsulfinylbenzylidene)-3-indenyl-γ-(β-ketobutyric) acid |
| cis-5-fluoro-6-methoxy-2-methyl-1-(4'-methylthiobenzylidene)-3-indenyl-γ-(β-hydroxybutyric) acid | cis-5-fluoro-6-methoxy-2-methyl-(4'-methylsulfinylbenzylidene)-3-indenyl-γ-(β-ketobutyric) acid |
| cis-5,7-difluoro-2-methyl-1-(4'-methylthiobenzylidene)-3-indenyl-γ-(β-hydroxybutyric) acid | cis-5,7-difluoro-2-methyl-1-(4'-methylsulfinylbenzylidene)-3-indenyl-γ-(β-ketobutyric) acid |
| cis-5-cyano-2-methyl-1-(4'-methylthiobenzylidene)-3-indenyl-γ-(β-hydroxybutyric) acid | cis-5-cyano-2-methyl-1-(4'-methylsulfinylbenzylidene)-3-indenyl-γ-(β-ketobutyric) acid |
| cis-5-methoxy-2-methyl-1-(4'-methylthiobenzylidene)-3-indenyl-γ-(β-hydroxybutyric) acid | cis-5-methoxy-2-methyl-1-(4'-methylsulfinylbenzylidene)-3-indenyl-γ-(β-ketobutyric) acid |
| cis-5-allyloxy-2-methyl-1-(4'-methylthiobenzylidene)-3-indenyl-γ-(β-hydroxybutyric) acid | cis-5-allyloxy-2-methyl-1-(4'-methylsulfinylbenzylidene)-3-indenyl-γ-(β-ketobutyric) acid |
| cis-5-acetyl-2-methyl-1-(4'-methylthiobenzylidene)-3-indenyl-γ-(β-hydroxybutyric) acid | cis-5-acetyl-2-methyl-1-(4'-methylsulfinylbenzylidene)-3-indenyl-γ-(β-ketobutyric) acid |
| cis-5,6-difluoro-1-(4'-methylthiobenzylidene)-3-indenyl-γ-(β-hydroxybutyric) acid | cis-5,6-difluoro-1-(4'-methylsulfinylbenzylidene)-3-indenyl-γ-(β-ketobutyric) acid |
| cis-5-fluoro-6-methoxy-1-(4'-methylthiobenzylidene)-3-indenyl-γ-(β-hydroxybutyric) acid | cis-5-fluoro-6-methoxy-(4'-methylsulfinylbenzylidene)-3-indenyl-γ-(βketobutyric) acid |
| cis-5,7-difluoro-1-(4'-methylthiobenzylidene)-3-indenyl-γ-(β-hydroxybutyric) acid | cis-5,7-difluoro-1-(4'-methylsulfinylbenzylidene)-3-indenyl-γ-(β-ketobutyric) acid |
| cis-5-cyano-1-(4'-methylthiobenzylidene)-3-indenyl-γ-(β-hydroxybutyric) acid | cis-5-cyano-1-(4'-methylsulfinylbenzylidene)-3-indenyl-γ-(β-ketobutyric) acid |
| cis-5-methoxy-1-(4'-methylthiobenzylidene)-3-indenyl-γ-(β-hydroxybutyric) acid | cis-5-methoxy-1-(4'-methylsulfinylbenzylidene)-3-indenyl-γ-(β-ketobutyric) acid |
| cis-5-allyloxy-1-(4'-methylthiobenzylidene)-3-indenyl-γ-(β-hydroxybutyric) acid | cis-5-allyloxy-1-(4'-methylsulfinylbenzylidene)-3-indenyl-γ-(β-ketobutyric acid |
| cis-5-acetyl-1-(4'-methylthiobenzylidene)-3-indenyl-γ-(β-hydroxybutyric) acid | cis-5-acetyl-1-(4'-methylsulfinylbenzylidene)-3-indenyl-γ-(β-ketobutyric) acid | zylidene)-3-indenyl-γ-(β-hydroxybutyric)acid

EXAMPLE 3

A.

Methyl-5-fluoro-2-methyl-3-indenyl-γ-(β-butynoate)

A mixture of 6-fluoro-2-methyl-1-indanone (24.6 g., 0.15 mole), "activated" zinc dust (12.7 g., 0.20 mole), methyl-4-bromo-3-butynoate (0.15 mole), and a crystal of iodine in dry benzene (750 ml.) is refluxed for 5 hours. The mixture is poured into 5% sulfuric acid (750 ml.), extracted with ether, the ether extract dried (MgSO₄) and the ethereal solution concentrated. The crude ester is redissolved in benzene (220 ml.), phosphorous pentoxide (44 g.) added, and the resulting mixture is refluxed for 30 minutes. The mixture is decanted, the residue washed with benzene, the benzene layers are combined, washed with water, saturated salt solution and dried (MgSO₄). Concentrations of dried organic phase yields methyl 5-fluoro-2-methyl-3-indenyl-γ-(β-butynoate) as a residue.

B. cis-and trans-5-Fluoro-2-methyl-1-(4'-methylthio-benzylidene)-3-indenyl-γ-(β-butynoic) Acids Methyl 5-fluoro-2-methyl-3-indenyl-γ-(β-butynoate) 0.0015 mole in methanol (15 ml.) is treated with sodium methoxide (0.162 g., 0.003 mole) and p-methylthiobenzaldehyde (0.342 g., 0.00225 mole) and the mixture heated at reflux for 5 hours. Water (10 ml.) is added and the new mixture refluxed for 1 hour more. The mixture is cooled to 25°, extracted with methylene chloride, the aqueous layer acidified to pH 2 and extracted with ether. The ethereal extract is dried (MgSO₄), and concentrated in vacuo to an oil. The oil is chromatographed over silica gel and eluted with methanolic chloroform to obtain cis- and trans-5-fluoro-2-methyl-1-(4'-methylthiobenzylidene)-3-indenyl-γ-(β-butynoic) acids.

C.

cis-5-Fluoro-2-methyl-1-(4'-methylsulfinylbenzylidene)-3-indenyl-γ-(β-butynoic) Acids To a solution of the cis-thio compound (0.600 g., 0.00168 mole) from Example 1-B in methanol (50 ml.), water (15 ml.) and acetone (50 ml.) is added sodium periodate (2 g.) in water (2 ml.). The mixture is allowed to stand. Each day for 3 successive days sodium periodate (2 grams) in water (2 ml.) is added.

On the fourth day saturated sodium chloride solution is added and the mixture extracted with methylene chloride, the organic phase dried (MgSO$_4$) and concentrated to a glass in vacuo. To the residue in methanol (100 ml.) is added concentrated sulfuric acid (1 ml.) and the mixture refluxed for 1 hour. The mixture is concentrated at room temperature in vacuo, the residue taken up in benzene and water, the benzene solution washed with water, 5% sodium bicarbonate and saturated salt solution. The benzene extract is dried (MgSO$_4$) and chromatographed on silica gel. The eluate with methanolic chloroform (1%) is concentrated to dryness in vacuo. The residue is saponified with sodium methoxide in methanol. The mixture is concentrated to dryness, taken up in ethyl acetate-water, the water layers acidified to pH 2 and the layers separated. The aqueous layer is extracted with ethyl acetate and the combined organic extracts dried (MgSO$_4$) and concentrated to dryness in vacuo. The residue is crystallized from acetone-n-hexane to yield cis-5-fluoro-2-methyl-1-(4'-methylsulfinyl-benzylidene)-3-indenyl-γ-(β-butynoic) acid.

EXAMPLE 4 cis-5-Fluoro-2-methyl-1-(4'-methylsulfinylbenzylidene)-γ-(γ-ketobutyric) acid

The acid (0.761 g., 0.002 mole) from Example 3 in ethyl acetate (60 ml.) is stirred with mercuric acetate (1.27 g., 0.004 mole) for 24 hours at 25°. Hydrogen sulfide is passed into the mixture to precipitate mercury as the sulfide. The mixture is filtered through diatomaceous earth, the residue washed with ethyl acetate, and the filtrate taken to dryness in vacuo. The residue is recrystallized from ethyl acetate-n-hexane to yield cis-5-fluoro-2-methyl-1-(4'-methylsulfinyl-benzylidene)-3-indenyl-γ-(γ-ketobutyric) acid.

Using the same reaction conditions and techniques as in Example 4, the following γ-(γ-ketobutyric) acids are obtained.

| STARTING MATERIAL | PRODUCT |
|---|---|
| cis-5-fluoro-2-methyl-1-(4'-methylsulfinylbenzylidene)-γ-(β-butynoic) acid | cis-5-fluoro-2-methyl-1-(4'-methylsulfinylbenzylidene)-γ-(γ-ketobutyric) acid |
| cis-5,6-difluoro-2-methyl-1-(4'-methylsulfinylbenzylidene)-γ-(β-butynoic) acid | cis-5,6-difluoro-2-methyl-1-(4'-methylsulfinylbenzylidene)-γ-(γ-ketobutyric) acid |
| cis-5-methoxy-6-fluoro-2-methyl-1-(4'-methylsulfinylbenzylidene)-γ-(β-butynoic) acid | cis-5-methoxy-6-fluoro-2-methyl-1-(4'-methylsulfinylbenzylidene)-γ-(γ-ketobutyric) acid |
| cis-5,7-difluoro-2-methyl-1-(4'-methylsulfinylbenzylidene)-γ-(β-butynoic) acid | cis-5,7-difluoro-2-methyl-1-(4'-methylsulfinylbenzylidene)-γ-(γ-ketobutyric) acid |
| cis-5-cyano-2-methyl-1-(4'-methylsulfinylbenzylidene)-γ-(β-butynoic) acid | cis-5-cyano-2-methyl-1-(4'-methylsulfinylbenzylidene)-γ-(γ-ketobutyric acid |
| cis-5-methoxy-2-methyl-1-(4'-methylsulfinylbenzylidene)-γ-(β-butynoic) acid | cis-5-methoxy-2-methyl-1-(4'-methylsulfinylbenzylidene)-γ-(γ-ketobutyric) acid |
| cis-5-allyloxy-2-methyl-1-(4'-methylsulfinylbenzylidene)-γ-(β-butynoic) acid | cis-5-allyloxy-2-methyl-1-(4'-methylsulfinylbenzyl=idene)-γ-(γ-ketobutyric) acid |
| cis-5-fluoro-1-(4'-methylsulfinylbenzylidene)-γ-(β-butynoic) acid | cis-5-fluoro-1-(4'-methylsulfinylbenzylidene)-γ-(γ-ketobutyric) acid |
| cis-5,6-difluoro-1-(4'-methylsulfinylbenzylidene)-γ-(β-butyric) acid | cis-5,6-difluoro-1-(4'-methylsulfinylbenzylidene)-γ-(γ-ketobutyric) acid |
| cis-5-methoxy-6-fluoro-1-(4'-methylsulfinylbenzylidene)-γ-(β-butynoic) acid | cis-5-methoxy-6-fluoro-1-(4'-methylsulfinylbenzylidene)-γ-(γ-ketobutyric) acid |
| cis-5,7-difluoro-1-(4'-methylsulfinylbenzylidene)-γ-(β-butynoic) acid | cis-5,7-difluoro-1-(4'-methylsulfinylbenzylidene)-γ-(γ-ketobutyric) acid |
| cis-5-cyano-1-(4'-methylsulfinylbenzylidene)-γ-(β-butynoic) acid | cis-5-cyano-1-(4'-methylsulfinylbenzylidene)-γ-(γ-ketobutyric) acid |
| cis-5-methoxy-1-(4'-methylsulfinylbenzylidene)-γ-(β-butynoic) acid | cis-5-methoxy-1-(4'-methylsulfinylbenzylidene)-γ-(γ-ketobutyric) acid |
| cis-5-allyloxy-1-(4'-methylsulfinylbenzylidene)-γ-(β-butynoic) acid | cis-5-allyloxy-1-(4'-methylsulfinylbenzylidene)-γ-(γ-ketobutyric) acid |

EXAMPLE 5

A. 3-Hydroxy-4-methylthiobenzaldehyde o-Hydroxythioanisole (0.35 mole) in methylene chloride (200 ml.) is added to anhydrous aluminum chloride (66.67 g., 0.5 mole). The mixture is stirred and cooled while dichloromethyl methyl ester is added dropwise. After the solution is completed, the mixture is stirred for 15 minutes at room temperature. The liquid phase is decanted into ice and water (300 g.) and the unreacted aluminum chloride is washed with methylene chloride until the washes are colorless. The washes and decanted material are combined. The layers are separated and the organic layer is washed with saturated potassium carbonate, dried (MgSO$_4$), and distilled to yield 3-hydroxy-4-methylthio-benzaldehyde. Similarly, when o-fluorothioanisole is used in the above example, there is obtained 3-fluoro-4-methylthiobenzaldehyde.

B. cir- and trans-5-Fluoro-2-methyl-l-(3'-hydroxy (4'-methylthiobenzylidene)-3-indenyl-γ-(β-hydroxybutyric) Acids Powdered sodium methoxide (22 g., 0.04 mole) is added to a suspension of methyl 5-fluoro-2-methyl-3-indenyl-γ-(β-hydroxybutyrate) 0.1 mole and 3-hydroxy-4-methylthiobenzaldehyde (15.2 g., 0.1 mole) in methanol (400 ml.), and the the mixture is heated at reflux for 2 hours. The mixture is stirred as sodium chloride precipitates to minimize bumping. An equal volume of water is added and refluxing continued for 1 hour. The mixture is cooled to room temperature and worked up as in Example 1-B to yield cis- and trans-5-fluoro-5-fluoro-2-methyl-l-(3'-hydroxy-4'-methylthiobenzylidene)-3-indenyl-γ-butyric acids. Similarly, when 3-fluoro-4-methylthiobenzaldehyde is used in place of 3-hydroxy-4-methylthiobenzaldehyde in the above example, there is obtained the corresponding 3-fluoro-4-methylthiobenzylidene compound.

C.

cis-5-Fluoro-2-methyl-l-(3'-hydroxy-4'-methylsulfinylbenzylidene)-3-indenyl -γ-(β-hydroxybutyric) Acid Sodium metaperiodate trihydrate (11.3 g., 0.0422 mole) in water (85 ml.) is added to cis-5-fluoro-2-methyl-l-(3'-hydroxy-4'-methylthiobenzylidene)-3-indenyl-γ-(β-hydroxybutyric) acid 0.01 mole in methanol (240 ml.) and acetone (10 ml.) at room temperature. The mixture is stirred overnight, after which only a trace of starting material remains and only a trace of sulfone has formed. The mixture is concentrated to small volume, diluted with water and filtered. The precipitate is washed well with water, dried in air; then in vacuo at 50° and recrystallized from ethyl acetate-n-hexane to yield cis-5-fluoro-2-methyl-l-(3'-hydroxy-4'-methylsulfinyl)-3-indenyl-γ-(β-hydroxy-butyric) acid. Similarly, when the 3-fluoro-4-methylthio-benzylidene compound obtained from Example 5B above is used in the above example, there is obtained the corresponding 3-fluoro-4-methylsulfinylbenzylidene compound.

Using the same reaction conditions and techniques, when o-chlorothioanisole, o-bromothioanisole and o-cyano-thioanisole are reacted according to steps A, B and C, there is obtained cis-5-fluoro-2-methyl-l-(3'-chloro-4'-methyl-sulfinylbenzylidene)-3-indenyl-γ-(β-hydroxybutyric) acid, cis-5-fluoro-2-methyl-l-(3'-bromo-4'-methylsulfinylbenzly-idene) -3-indenyl-γ-(β-hydroxybutyric) acid and cis-5-fluoro-2-methyl-l-(3'-cyano-4'-methylsulfinylbenzylidene)-3-indenyl-γ-(β-hydroxybutyric) acid.

EXAMPLE 6

A. o-(β-Hydroxyethoxy)-thioanisole o-Hydroxythioanisole (14.1 g., 0.1 mole) is dissolved in sodium ethoxide (6.8 g., 0.1 mole) in absolute ethanol (100 ml.) and stirred as β-hydroxyethyl chloride (8.1 g., 0.1 mole) is added. The reaction mixture is refluxed for 2 hours and cooled. The o-(β-hydroxyethoxy)-thioanisole is extracted.

Using the same reaction conditions and techniques, when o-hydroxythioanisole is reacted with β-hydroxymethyl chloride, β-hydroxypropyl chloride or β-hydroxybutyl chloride, there is obtained o-(β-hydroxymethoxy)-thioanisole, o-(β-hydroxypropoxy)-thioanisole and o-(βhydroxybutoxy)-thioanisole, respectively.

B.
cis-5-Fluoro-2-methyl-l-(3'-β-hydroxyethoxy-4'-methylsulfinylbenzylidene)-3-indenyl-γ-(β-hydroxybutyric) Acid The product of Example 6-A is reacted by the methods of Examples 5-A, 5-B and 5-C to obtain cis-5-fluoro-2-methyl-l-(3'-β-hydroxyethoxy-4'-methylsulfinyl-benzylidene)-3-indenyl-γ-(β-hydroxybutyric) acid.

In this manner the other thioanisoles of Example 15-A may be reacted to form the corresponding 3-indenyl-γ-(β-hydroxybutyric) acid.

EXAMPLE 7

A. o-(β-Chloroethoxy)-thioanisole o-(β-Hydroxyethoxy)-thioanisole (0.1 mole) is refluxed in excess thionyl chloride and evaporated to dryness to yield o-(β-chloroethoxy)-thioanisole.

In a like manner, other o-(βhydroxyalkoxy)-thioanisoles may be refluxed with other thionyl halides to yield the appropriate o-(β-haloalkoxy)-thioanisole as, for example, o-(β-bromomethoxy)-thioanisole, o-(β-chloro-propoxy)-thioanisole, or o-(β-bromobutoxy)-thioanisole.

B.
cis-5-Fluoro-2-methyl-l-(3'-β-chloroethoxy-4'-methylsulfinylbenzylidene)-3-indenyl-γ-(β-hydroxybutyric) Acid The product of Example 7-A is reacted by the methods of Examples 5A, 5-B and 5C to obtain cis-5-fluoro-2-methyl-l-(3'-β-chloroethoxy-4'-methylsulfinyl-benzylidene)-3-γ-(β-hydroxybutyric) acid.

In this manner the other thioanisoles of Example 7-A may be reacted to form the corresponding indenyl-γ-(β-hydroxybutyric) acids.

EXAMPLE 8

A. o-Ethoxythioanisole o-Chlorothioanisole (prepared by the procedure of Example 5-A (15.85 g., 0.1 mole) is stirred at reflux in nitrobenzene containing copper powder (100 mg.) and sodium ethoxide (6.8 g., 0.1 mole) for 2 hours. The product is steam distilled and the distillate dried and fractionally distilled under reduced pressure to yield o-ethoxythioanisole.

Using the same reaction conditions and techniques, when o-chlorothioanisole is reacted with sodium methoxide, sodium propoxide and sodium t-butoxide, there are obtained o-methoxythioanisole, o-propoxythioanisole and o-t-butoxy-thioanisole, respectively.

B.
cis-5-Fluoro-2-methyl-l-(3'ethoxy-4'-methylsulfinylbenzylidene)-3-indenyl-γ-(β-hydroxybutyric) Acid The product of Example 8A is reacted by the methods of Examples 5-A, 5-B and 5-C to obtain cis-5-fluoro-2-methyl-l-(3'-ethoxy-4'-methylsulfinylbenzylidene)-3-indenyl-γ-(β-hydroxybutyric) acid.

In this manner the other thioanisoles of Example 8-A may be reacted to form the corresponding indenyl-γ-(β-hydroxybutyric) acids.

EXAMPLE 9

Methyl cis-5-fluoro-2-methyl-l-(3', 4'-bismethylsulfinyl-benzylidene)-3-indenyl-γ-(β-hydroxybutyrate)

cis-5-Fluoro-2-methyl-l-(3', 4'-bismethylsulfinyl-benzylidene-3-indenyl-γ-(β-hydroxybutyric) acid (0.03 mole) is dissolved in methanol (50 ml.), concentrated sulfuric acid (1.0 ml.) is added and the mixture heated at reflux for 3 hours. The mixture is cooled, poured into ethyl acetate and extracted successively with saturated sodium bicarbonate, water and saturated salt solution. The ethyl acetate extract is dried (MgSO₄), concentrated to dryness and the residue crystallized from ethyl acetate-n-hexane. Similarly, when the other acids of Examples 1–8 are reacted in accordance with Example 9 above, the corresponding methy esters are obtained. Similarly, the propyl, β-chloropropyl or acetyl-oxyethyl esters are obtained when employing propyl alcohol, β-chloropropyl alcohol or acetyloxyethanol in place of methanol.

EXAMPLE 10 cis-5-Fluoro-2-methyl-l-(3'-fluoro-4'-methylsulfinylbenzylidene)-3-indenyl-γ-(β-hydroxybutamide)

cis-5-Fluoro-2-methyl-l-(3'fluoro-4'-methyl-sulfinyl-benzylidene)-3-indenyl-γ-(β-hydroxybutyric) acid (0.01 mole) is warmed with thionyl chloride (5 ml.) for 25 minutes. The mixture is cooled to 25° and poured with stirring into ice-cold concentrated ammonia solution. The precipitated amide is washed with water, dried and recrystallized from methanol-water to yield cis-5-fluoro-2-methyl-l-(3'-fluoro-(4'-methylsulfinyl-benzylidene)-3-indenyl-γ-(β-hydroxybutamide).

Similarly, when ammonia is replaced by an equivalent amount of the following amines, the corresponding amides are obtained:
Morpholine
Dimethylamine
Ethanolamine Benzylamine
N,N-diethylethylenediamine
Benzylglycinate
Piperidine
Pyrrolidine
N-methylpiperazine
N-phenylpiperazine
N-hydroxyethylpiperazine
Piperazine
Diethylamine
Diethanolamine
Aniline
p-Ethoxyaniline
p-Chloroaniline
p-Fluoroaniline
p-Trifluoromethylaniline
Butylamine
Cyclohexylamine
Methylamine
D-glucosamine
Tetra-o-acetyl-d-glucosamine
D-galactosylamine
D-mannosylamine
N,N-dimethylglycine amide
N,N-dibutylglycine amide
N-methyl-2-aminomethylpiperidine
N-methyl-2-aminomethylpyrrolidine
β-Ethoxyethylamine
Di(β-ethoxyethyl) amine
β-Phenethylamine
α-Phenethylamine
Dibenzylamine
D-mannosamine Similarly, when the other acids of Examples 1–8 are used in accordance with Example 10, the corresponding amides are obtained.

EXAMPLE 11 t-Butyl cis-5-Fluoro-2-methyl-1-(4′methylsulfinyl-benzylidene)-3-indenyl-γ-(β-ketobutyrate)

cis-5-Fluoro-2-methyl-1-(4′methylsulfinyl-benzylidene)-3-indenyl-γ-butyric acid (0.01 mole) is added to isobutylene (30 ml.) and concentrated sulfuric acid (0.1 ml.). The mixture is stoppered securely and shaken at 25° for 18 hours, chilled to 0° and the whole poured into a separatory funnel containing ether (50 ml.); water (25 ml.), ice (25 ml.) and sodium hydroxide (1.0 g.). The layers are separated, the water layer extracted with ether (2 × 40 ml.), the ethereal extracts washed with water and saturated salt solution and dried (MgSO₄). The ethereal extract is concentrated to dryness and the residue crystallized from ethyl acetate-n-hexane to yield the subject compound.

EXAMPLE 12

Ammonium cis-5-Allyloxy-2-methyl-1-(4′methylsulfinyl-benzylidene)-3-indenyl-γ-(β-hydroxybutyrate)

To cis-5-allyloxy-2-methyl-1-(4′methyl-sulfinylbenzylidene)-3-indenyl-γ-(β-hydroxybutyric) acid (0.001 mole) in methanol (10 ml.) is added methanolic ammonia (1 N, 1 ml.). The mixture is evaporated to dryness to yield the subject compound.

EXAMPLE 13

Calcium cis-5-Fluoro-2-methyl-1-(4′-methylsulfinylbenzylidene)-3-indenyl-γ-(β-hydroxybutyrate)

To a slurry of cis-5-fluoro-2-methyl-1-(4′-methylsulfinylbenzylidene)-3-indenyl-γ-(β-hydroxybutyric) acid (0.002 mole) in water (10 ml.) is added hydrated calcium oxide (0.076 g., 0.001 mole) and the mixture stirred for 15 minutes. The mixture is concentrated to dryness in vacuo, slurried with methanol (10 ml.) and again concentrated to dryness to yield the subject compound.

EXAMPLE 14

Aluminum cis-5-Acetyl-2-methyl-1-(4′methylsulfinylbenzylidene-3-indenyl-γ-(α-ketobutyrate)

To a solution of aluminum tert-butoxide (0.246 g., 0.001 mole) in ether (50 ml.) is added cis-5-acetyl-2-methyl-1-(4′methylsulfinylbenzylidene)-3-indenyl-γ-(α-ketobutyric) acid (0.003 mole) in pyridine (50 ml.) with stirring at 10°. The mixture is concentrated to dryness in vacuo to yield the subject compound.

EXAMPLE 15

Sodium cis-5-Fluoro-2-methyl-1-(4′methylsulfinylbenzylidene)-3-indenyl-γ-(α-hydroxybutyrate)

To cis-5-fluoro-2-methyl-1-(4′-methylsulfinyl-benzylidene)-3-indenyl-γ-(α-hydroxybutyric) acid (0.001 mole) in methanol is added methanolic sodium methoxide (0.1 N, 10 ml.). The mixture is concentrated to dryness in vacuo to yield the subject compound.

EXAMPLE 16

Methoxymethyl cis-5-allyloxy-2-methyl-1-(p-methyl-sulfinylbenzylidene)-3-indenyl-γ-(α-hydroxybutyrate)

Chloromethyl methyl ether (0.055 mole) is added to a suspension of cis-5-allyloxy-2-methyl-1-(p-methyl-sulfinylbenzylidene)13-indenyl-γ-(β-hydroxybutyric) acid (0.05 mole) and anhydrous potassium carbonate (0.15 mole) in 250 ml. of anhydrous acetone. The mixture is allowed to stir overnight at room temperature. Diethyl ether is added (about 200 ml.) and the mixture is filtered. The filtrate is washed once with 100 ml. of water and dried over anhydrous sodium sulfate. It is then filtered and the solvent is removed in vacuo. The residue is chromatographed on 200 g. of acid-washed alumina, using ether-petroleum ether (varying from 10–60% ether by volume) as the eluent, to give methoxymethyl cis-5-allyloxy-2-methyl-1-(p-methylsulfinylbenzylidene)-3-indenyl-γ-(α-hydroxybutyrate).

EXAMPLE 17

β-Diethylaminoethyl cis-5-allyloxy-2-methyl-1-(p-methylsulfinylbenzylidene)-3-indenyl-γ-(β-hydroxybutyrate)

A solution of 0.0054 mole of N,N′-dicyclohexylcarbodiimide in 6 ml. of anhydrous tetrahydrofuran is added to a solution of cis-5-fluoro-2-methyl-1-(p-methylsulfamylbenzylidene)-3-indenyl-γ-(β-hydroxybutyric) acid (0.005 mole) and 2-diethylaminoethanol (0.0054 mole) in 17 ml. of anhydrous tetrahydrofuran. The mixture is stirred at ambient temperaturer overnight. The dicyclohexylurea is removed by filtration and 2 ml. of glacial acetic acid is added to the filtrate. After the mixture has stood for 1 hour, it is filtered and 200 ml. of ether is added to the filtrate. The solution is then extracted three times with 100 ml. of 2.5 N HCl and the extracts are combined, washed twice with 100 ml. of ether, ice-cooled, made slightly alkaline with concentrated $NH_4OH$ and extracted three times with 100 ml. of ether. The ether extracts are combined, washed 10 times with 100 ml. of water to remove traces of starting amine, dried over anhydrous potassium carbonate, filtered, and evaporated in vacuo. The oily residue is β-diethylaminoethyl cis-5-allyloxy-2-methyl-1-(p-methylsulfinylbenzylidene)-3-indenyl-γ-(β-hydroxy-butyrate).

When 2-dimethylaminoethanol, 3-dimethylamino-l-propanol, 3-diethylamino-l-propanol, N-β-hydroxyethylpiperidine, N-β-hydroxethylpyrrolidine, N-hydroxymethylpyrrolidine, N-methyl-2-hydroxymethylpyrrolidine, N-ethyl-2-hydroxymethylpiperidine, 1-β-hydroxyethyl-4′-methylpiperazine or N-β-hydroxyethyl morpholine is used in the above procedure in place of 2-diethylaminoethanol, the corresponding β-dimethylaminoethyl, γ-dimethylaminopropyl, γ-diethylaminopropyl, β-N-piperidinylethyl, β-N-pyrrolidinylethyl, N-pyrrolidinylmethyl, α′-(1′methyl-pyrrolidinylmethyl), 4-methyl-1-piperazinylethyl, N-ethyl-2-piperidinylethyl and N-morpholinylethyl esters are obtained.

EXAMPLE 18

5-Fluoro-2-methyl-1-(p-methylsulfinylbenzylidene)-indenyl-γ-(γ-hydroxybutyric) acid 5-Fluoro-2-methyl-l-(p-methylsulfinylbenzylidene)-indenyl-γ-(γ-ketobutyric acid (0.1 mole) is stirred in aqueous alcoholic solution (20 ml. ethanol, 10 ml. water) while sodium borohydride (0.13 mole) is dropped in over 10 minutes. The reaction mixture is stirred for 30 minutes. The alcohol evaporated off under high vacuo at 40°. The reaction mixture is acidified with 2.5N HCl and the 5fluoro-2-methyl-1-(p-methylsulfiinylbenzylidene)-indenyl-γ-(γ-hydroxylbutyric) acid filtered off.

In the above manner the following γ-hydroxy and β-hydroxybutyric acids are made:

| STARTING MATERIAL | PRODUCT |
|---|---|
| 5-Fluoro-2-methyl-1-(p-methylsulfinylbenzylidene)-indenyl-γ-(γ-ketobutyric) acid | 5-Fluoro-2-methyl-1-(p-methylsulfinylbenzylidene)-indenyl-γ-(γ-hydroxybutyric) acid |
| 5-Fluoro-2-methyl-1-(p-methylsulfonylbenzylidene)-indenyl-γ-(γ-ketobutyric) acid | 5-Fluoro-2-methyl-1-(p-methylsulfonylbenzylidene)-indenyl-γ-(γ-hydroxybutyric) acid |
| 5-Cyano-2-methyl-1-(p-methylsulfinylbenzylidene)-indenyl-γ-(γ-ketobutyric) acid | 5-Cyano-2-methyl-1-(p-methylsulfinylbenzylidene)-indenyl-γ-(γ-hydroxybutyric) acid |
| 5-Fluoro-2-methyl-1-(p-methylsulfinylbenzylidene)-indenyl-γ-(β-ketobutyric) acid | 5-Fluoro-2-methyl-1-(p-methylsulfinylbenzylidene)-indenyl-γ-(β-hydroxybutyric) acid |
| 5-Fluoro-2-methyl-1-(p-methylthiobenzylidene)-indenyl-γ-(β-ketobutyric) acid | 5-Fluoro-2-methyl-1-(p-methylthiobenzylidene)-indenyl-γ-(β-hydroxybutyric) acid |
| 6-Fluoro-2-methyl-1-(p-methylsulfinylbenzylidene)-indenyl-γ(γ-ketobutyric) acid | 6-Fluoro-2-methyl-1-(p-methylsulfinylbenzylidene)-indenyl-γ-(γ-hydroxybutyric) acid |
| 6-Fluoro-2-methyl-1-(p-methylthiobenzylidene)-indenyl-γ-(γ-ketobutyric) acid | 6-Fluoro-2-methyl-1-(p-methylthiobenzylidene)-indenyl-γ-(γ-hydroxybutyric) acid |
| 5-Dimethylamino-2-methyl-1-(p-methylsulfinylbenzylidene)-indenyl-γ-(γ-ketobutyric) acid | 5-Dimethylamino-2-methyl-1-(p-methylsulfinylbenzylidene)-indenyl-γ-(γ-hydroxybutyric) acid |
| 5-Allyloxy-2-methyl-1-(p-methylsulfinylbenzylidene)-indenyl-γ-(γ-ketobutyric) acid | 5-Allyloxy-2-methyl-1-(p-methylsulfinylbenzylidene)-indenyl-γ-(γ-hydroxybutyric) acid |
| 5-Ethynyl-2-methyl-1-(p-methylsulfinylbenzylidene)-indenyl-γ-(γ-ketobutyric) acid | 5-Ethynyl-2-methyl-1-(p-methylsulfinylbenzylidene)-indenyl-γ-(γ-hydroxybutyric) acid |

EXAMPLE 19

A mixture of 250 parts of 5-fluoro-2-methyl-1-(4′-methylsulfinylbenzylidene)-3-indenyl-γ-(γ-ketobutyric) acid and 25 parts of lactose is granulated with suitable water and to this is added 100 parts of maize starch. The mass is passed through a 16 mesh screen. The granules are dried at a temperature below 60°C. The dried granules are passed through a 16 mesh screen and mixed with 3.8 parts of magnesium stearate. They are then compressed into tablets suitable for oral administration according to the method of this invention.

Similarly, when any of the other butyric acid compounds of Examples 1–18 are used in the above example, tablets are obtained for oral administration in accordance with this invention.

What is claimed is:

1. A compound of the formula

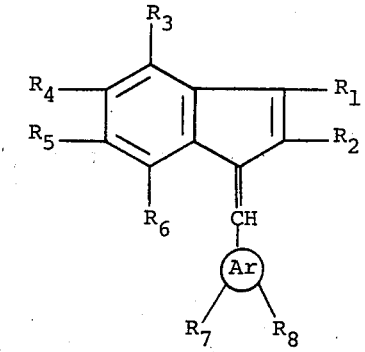

wherein $R_1$ is

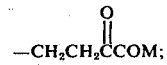

$R_2$ is hydrogen or $C_{1-15}$ alkyl;

Ar is phenyl;

$R_3$, $R_4$, $R_5$ and $R_6$ each may be hydrogen, nitro, amino, sulfamyl, mercapto, hydroxy, halogen, cyano, carboxyl, carbamido, $C_{1-5}$ alkyl, $C_{1-5}$ alkoxy, $C_{1-5}$ alkanoyl, $C_{1-5}$ alkenyloxy, $C_{1-5}$ alkanoyloxy, dimethylamino or ethynyl;

$R_7$ is $C_{1-5}$-alkylsulfinyl, $C_{1-5}$ alkylsulfonyl or methylthio;

$R_8$ is hydrogen, halogen, hydroxy, $C_{1-5}$ alkoxy or $C_{1-5}$ haloalkoxy; and M is hydroxy, $C_{1-5}$ alkoxy, $C_{1-5}$ alkanoyloxy-$C_{1-5}$ alkoxy or OMe in which Me is a cation of a pharmaceutically acceptable salt; provided that at least one of $R_3$, $R_4$, $R_5$ and $R_6$ is not hydrogen.

2. A compound as in claim 1 wherein $R_1$ is

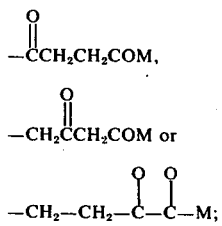

$R_2$ is hydrogen or $C_{1-5}$ alkyl;
$R_3$ is hydrogen;
$R_4$ is halogen, $C_{1-5}$ alkoxy or allyloxy;
$R_5$ and $R_6$ are hydrogen;
$R_7$ is $C_{1-5}$ alkylsulfinyl, $C_{1-5}$ alkylsulfonyl or methylthio;
$R_8$ is hydrogen, halogen, hydroxy, $C_{1-5}$ alkoxy or $C_{1-5}$ kaloalkoxy; and
M is hydroxy, $C_{1-5}$ alkoxy, $C_{1-5}$ alkanoyloxy-$C_{1-5}$ alkoxy or OMe in which Me is ammonium, calcium, aluminum or sodium.

3. The compound of claim 1 wherein $R_1$ is

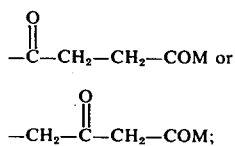

$R_2$ is hydrogen or $C_{1-5}$ alkyl;
$R_3$, $R_4$, $R_5$ and $R_6$ are each hydrogen, $C_{1-5}$ alkyl, $C_{1-5}$ alkoxy, halogen, cyano, $C_{1-5}$ alkanoyl or $C_{2-5}$ alkenyloxy, at least two of $R_3$, $R_4$, $R_5$ and $R_6$ being hydrogen at any one time;
$R_7$ is $C_{1-5}$ alkylsulfinyl, $C_{1-5}$ alkylsulfinyl, $C_{1-5}$ alkylsulfonyl or methylthio;
$R_8$ is hydrogen, hydroxy, $C_{1-5}$ alkoxy, $C_{1-5}$ haloalkoxy or fluoro; and
M is hydroxy.

4. The cis- and trans- isomers of a compound as in claim 3.

5. A compound as in claim 3 wherein $R_1$ is

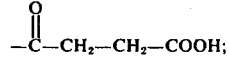

$R_2$ is methyl;
$R_3$ is hydrogen;
$R_4$ is fluoro;
$R_5$ and $R_6$ are hydrogen;
$R_7$ is methylsulfinyl; and
$R_8$ is hydrogen.

6. The compound of claim 3 wherein $R_1$ is

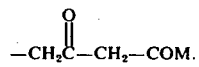

7. A compound as in claim 3 wherein $R_1$ is

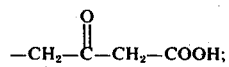

$R_2$ is methyl;
$R_3$ is hydrogen;
$R_4$ is fluoro;
$R_5$ and $R_6$ are hydrogen;
$R_7$ is methylsulfinyl; and
$R_8$ is hydrogen.

* * * * *

UNITED STATES PATENT OFFICE
CERTIFICATE OF CORRECTION

PATENT NO. : 3,932,498

DATED : January 13, 1976

INVENTOR(S) : Tsung-Ying Shen, Howard Jones and Michael Fordice

It is certified that error appears in the above-identified patent and that said Letters Patent are hereby corrected as shown below:

In column 20, line 58, "$C_{1-15}$alkyl" should be "$C_{1-5}$alkyl".

In column 20, line 63, "$C_{1-5}$alkenyloxy" should be "$C_{2-5}$alkenyloxy".

In column 21, the formula appearing between lines 14-16 should have two __double__ bonds.

In column 21, line 25, "kaloalkoxy" should be "haloalkoxy".

In column 22, line 3, "$C_{1-5}$alkylsulfinyl" should be deleted since it appears twice.

Signed and Sealed this twentieth Day of April 1976

[SEAL]

Attest:

RUTH C. MASON
Attesting Officer

C. MARSHALL DANN
Commissioner of Patents and Trademarks